US009371560B2

(12) United States Patent
Choudhary et al.

(10) Patent No.: US 9,371,560 B2
(45) Date of Patent: *Jun. 21, 2016

(54) COMPREHENSIVE FMR1 GENOTYPING

(71) Applicant: Asuragen, Inc, Austin, TX (US)

(72) Inventors: Ashish Choudhary, Austin, TX (US); Gary Latham, Austin, TX (US); Sachin Sah, Austin, TX (US)

(73) Assignee: Asuragen, Inc., Austin, TX (US)

( * ) Notice: Subject to any disclaimer, the term of this patent is extended or adjusted under 35 U.S.C. 154(b) by 6 days.

This patent is subject to a terminal disclaimer.

(21) Appl. No.: 13/946,544

(22) Filed: Jul. 19, 2013

(65) Prior Publication Data

US 2014/0024035 A1    Jan. 23, 2014

Related U.S. Application Data

(60) Provisional application No. 61/674,167, filed on Jul. 20, 2012.

(51) Int. Cl.
*C12Q 1/68*  (2006.01)
*G06F 19/18*  (2011.01)

(52) U.S. Cl.
CPC ............. *C12Q 1/6844* (2013.01); *G06F 19/18* (2013.01)

(58) Field of Classification Search
None
See application file for complete search history.

(56) References Cited

U.S. PATENT DOCUMENTS

| | | | |
|---|---|---|---|
| 4,683,202 A | 7/1987 | Mullis | |
| 5,648,211 A | 7/1997 | Fraiser et al. | |
| 5,658,764 A | 8/1997 | Pergolizzi et al. | |
| 5,843,730 A | 12/1998 | Wain-Hobson et al. | |
| 5,976,842 A | 11/1999 | Wurst | |
| 6,143,504 A | 11/2000 | Das et al. | |
| 6,200,747 B1 | 3/2001 | Pergolizzi et al. | |
| 6,287,824 B1 | 9/2001 | Lizardi | |
| 6,326,173 B1 | 12/2001 | Edman et al. | |
| 6,335,165 B1 | 1/2002 | Navot et al. | |
| 6,410,278 B1 | 6/2002 | Notomi et al. | |
| 6,670,124 B1 | 12/2003 | Chow et al. | |
| 6,881,559 B2 | 4/2005 | Sobek et al. | |
| 7,030,220 B1 | 4/2006 | Ankenbauer et al. | |
| 8,409,805 B2 | 4/2013 | Latham | |
| 8,679,757 B2 * | 3/2014 | Latham et al. ............... 435/6.12 |
| 2007/0207463 A1 | 9/2007 | Liu et al. | |
| 2008/0113355 A1 | 5/2008 | Hagerman et al. | |
| 2008/0124709 A1 | 5/2008 | Huang et al. | |
| 2008/0176293 A1 | 7/2008 | Rohayem et al. | |
| 2010/0209970 A1 | 8/2010 | Latham | |
| 2010/0243451 A1 | 9/2010 | Latham | |
| 2012/0107824 A1 | 5/2012 | Latham et al. | |

FOREIGN PATENT DOCUMENTS

| | | |
|---|---|---|
| AU | 1992014136 | 9/1992 |
| AU | 671418 | 8/1996 |
| WO | WO 92/14840 | 9/1992 |
| WO | WO 93/15225 A1 | 8/1993 |
| WO | WO 00/43531 | 7/2000 |
| WO | WO 2008/011170 | 1/2008 |
| WO | WO 2010/093552 A1 | 8/2010 |
| WO | WO 2010/110835 A1 | 9/2010 |
| WO | WO 2012/058633 A1 | 5/2012 |

OTHER PUBLICATIONS

Afonina et al., "Primers with 5' flaps improve real-time PCR," BioTechniques 43, 770 (2007).
Ayyagari et al., "FEN1 is a structure-specific nuclease that cleaves substrates containing unannealed 5'-flaps" J. Biol. Chem. 278, 1618-1625 (2003).
Bachinski et al., "Confirmation of the Type 2 Myotonic Dystrophy (CCTG)n Expansion Mutation in Patients with Proximal Myotonic Myopathy/Proximal Myotonic Dystrophy of Different European Origins: A Single Shared Haplotype Indicates an Ancestral Founder Effect," Am. J. Hum, Genet. 73:835-848 (2003).
Baskaran et al., "Uniform Amplification of a Mixture of Deoxyribonucleic Acids with Varying GC Content," Genome Res. 6:633-638 (1996) by Cold Spring Harbor Laboratory Press.
Bell et al., "Physical mapping across the fragile X: hypermethylation and clinical expression of the fragile X syndrome," Cell 64:861-866 (1991).
Bionexus, Inc. "All Purpose Hi-Lo DNA Marker/Mass Ladder" (2009).
Blazej et al., "Microfabricated Bioprocessor for Integrated Nanoliter-Scale Sanger DNA Sequencing," Proc. Natl. Acad. Sci. USA 103:7240-7245 (2006).
Bodega et al., "Influence of intermediate and uninterrupted FMR1 CGG expansions in premature ovarian failure manifestation," Hum. Reprod., 21(4): 952-957 (2006).
Brown et al., "Prenatal diagnosis and carrier screening for fragile X by PCR," American Journal of Medical Genetics 64:191-195 (1996).
Brown et al., "Rapid fragile X carrier screening and prenatal diagnosis using a nonradioactive PCR test," Journal of the American Medical Association, 270:1569-1575 (1993).
Cadwell et al., "Randomization of Genes by PCR Mutagenesis," PCR Methods Appl. 2:28-33 (1992) by Cold Spring Harbor Laboratory Press.
Cagnoli et al., "Detection of Large Pathogenic Expansions in FRDA1, SCA10, and SCA12 Genes Using a Simple Fluorescent Repeat-Primed PCR Assay," J. Mol. Diagn. 6:96-100 (2004)
Cagnoli et al., "Large Pathogenic Expansions in the SCA2 and SCA7 Genes Can Be Detected by Fluorescent Repeat-Primed Polymerase Chain Reaction Assay," J. Mol. Diagn. 8:128-132 (2006).

(Continued)

*Primary Examiner* — Stephanie K Mummert
(74) *Attorney, Agent, or Firm* — Finnegan, Henderson, Farabow, Garrett & Dunner, LLP

(57) ABSTRACT

Disclosed herein are methods for the automated reconstruction of a genotype of a gene, fragment, or genomic region using exhaustive enumeration. The methods can be used to reconstruct the genotype of any GC-rich sequence, such as the CGG repeat region in the 5' UTR of FMR1 or the CCG repeat region in the 5' UTR of FMR2. Also disclosed is an apparatus for use in conducting automated genotype reconstruction, as well as methods of diagnosis and treatment using exhaustive enumeration methods to reconstruct and identify genotypes associated with a disease or disorder.

25 Claims, No Drawings

(56) References Cited

OTHER PUBLICATIONS

Cao et al., "A simple fragile X PCR assay with 7-deazaguanine-substituted DNA visualized by ethidium bromide," Molecular and Cellular Probes 8:177-180 (1994).
Chen et al., "An Information-rich CGG repeat primed PCR that detects the full range of fragile X expanded alleles and minimizes the need for southern blot analysis", J. Mol. Diagn., 12:5, pp. 589-600, 2010.
Chiu et al., "The AGG interruption pattern within the CGG repeat of the FMR1 gene among Taiwanese population," Journal of Genetics, 87(3): 275-277 (2008).
Chong et al., "Robust amplification and ethidium-visible detection of the fragile X syndrome CGG repeat using Pfu polymerase." American Journal of Medical Genetics 51:522-526 (1994).
Ciotti et al., "Triplet Repeat Primed PCR (TP PCR) in Molecular Diagnostic Testing for Friedreich Ataxia," J Mol. Diag. 6:285-289 (2004).
Cirino et al,, "Generating Mutant Libraries Using Error-Prone PCR," Methods Mol. Biol. 231:3-9 (2003).
Cline et al., "PCR Fidelity of Pfu DNA Polymerase and Other Thermostable DNA Polymerases," Nucleic Acids Res. 24:3546-3551 (1996).
Dean et al., "Instability in the Transmission of the Myotonic Dystrophy CTG Repeat in Human Oocytes and Preimplantation Embroyos," Fertil. Steril. 86:98-105 (2006).
Debacker et al., "The molecular basis of the folate-sensitive fragile site FRA11A at 11q13," Cytogenetic and Genome Research 119:9-14 (2007).
Deiman et al., "Efficient Amplification with NASBA® of Hepatitis B Virus, Herpes Simplex Virus and Methicillin Resistant *Staphylococcus aureus* DNA," J. Viral, Methods 151:283-293 (2008).
Dewoody et al., "Universal Method for Producing ROX-labeled Size Standards Suitable for Automated Genotyping," Biotechniques, 37:348, 350, 352 (2004).
Dombrowski et al., "Premutation and Intermediate-Size FRM1 Alleles in 10 572 Males from the General Population: Loss of an AGG Interruption is a Late Event in the Generation of Fragile X Syndrome Alleles," Hum. Mol. Genet. 11:371-378 (2002).
Dorschner et al., "Diagnosis of Five Spinocerebellar Ataxia Disorders by Multiplex Amplification and Capillary Electrophoresis," J. Mol. Diag. 4:108-113 (2002).
Eckert, K. and T. Kunkel, PCR: A Practical Approach (The Practical Approach Series), Oct. 10, 1991, Chapter 14, pp. 225-246, Oxford University Press.
Eichler et al., "Length of Uninterrupted CGG Repeats Determines Instability in the FMR1 Gene," Nat. Genet. 8:88-94 (1994).
Eichler et al., "Population Survey of the human FMR1 CGG repeat substructure suggests biased polarity for the loss of AGG interruptions," Human Molecular Genetics, 4(12)2199-2208 (1995).
Erster et al., "Polymerase chain reaction analysis of fragile X mutations," Human Genetics 90:55-61 (1992).
Fernandez-Carvajal et al., "Expansion of an FMR1 grey-zone allele to a full mutation in two generations," Journal of Molecular Diagnostics 11(4):306-310 (2009).
Filipovic-Sadic et al., "A Novel FMR1 PCT Method for the Routine Detection of Low Abundance Expanded Alleles and Full Mutations in Fragile X Syndrome", Clinical Chemistry, 56:3, pp. 399-408, 2010.
Frey, UH. et al. "PCR-amplification of GC-rich regions: 'slowdown PCR'" Nature Protocols, vol. 3, No. 8, pp. 1312-1317, published online Jul. 2008.
Fromant et al., "Direct Random Mutagenesis of Gene-Sized DNA Fragments Using Polymerase Chain Reaction," Anal. Biochem. 224:347-353 (1995).
Fu et al., "Variation of the CGG repeat at the fragile X site results in genetic instability: resolution of the Sherman paradox," Cell 67:1047-1058 (1991).
Gecz et al., "Identification of the Genes FMR2, Associated with FRAXE Mental Retardation," Nat. Genet. 13:105-108 (1996).

Griep, M. et al. DNA polymerase chain reaction: a model of error frequencies and extension rates. AlChE Journal, 52(1):384-392 (2006).
Gruegelsiepe, H. et al., Handbook of RNA Biochemistry, May 6, 2005, Wiley-VCH, Weinheim, Germany, Chapter 1, pp. 1-21.
Gu et al., "Identification of FMR2, a Novel Gene Associated with the FRAXE CCG Repeat and CpG Island," Nat. Genet. 13:109-113 (1996).
Hadd et al., "Two Novel PCR Strategies that Amplify and Accurately Report the Full Range of FMR1 Genotypes without the Need for Southern Blot," poster presentation dated Nov. 23, 2009.
Haddad et al., "A PCR-Based Test Suitable for Screening for Fragile X Syndrome Among Mentally Retarded Males," Hum. Genet. 97:808-812 (1996).
Hamdan et al., "Automated Detection of Trinucleotide Repeats in Fragile X Syndrome," Molecular Diagnosis 2:259-269 (1997).
Hecimovic et al., "A simple and rapid analysis of triplet repeat diseases by expand long PCR," Clinical Chemistry and Lab Medicine 39(12):1259-1262 (2001).
Henke et al., "Betaine Improves the PCR Amplification of GC-Rich DNA Sequences," Nucleic Acids Res. 25:3957-3958 (1997).
Hirst et al., "Precursor Arrays for Triplet Repeat Expansion at the Fragile X Locus," Hum. Mol. Genet. 3:1553-1560 (1994).
Houdayer et al., "Improved fluorescent PCR-based assay for sizing CGG repeats at the FRAXA locus," Clinical Chemistry and Lab Medicine 37(4): 397-402 (1999).
Innis et al., "DNA Sequencing with Thermus Aquaticus DNA Polymerase and Direct Sequencing of Polymerase Chain Reaction-Amplified DNA," Proc. Natl. Acad. Sci. USA 85:9436-9440 (1988).
International Preliminary Report on Patentability and Written Opinion for International Application No. PCT/US2010/000426, dated Sep. 27, 2011.
International Search Report and Written Opinion, for International Application No. PCT/US2010/000426, dated Jul. 29, 2010.
International Preliminary Report on Patentability and Written Opinion for International Application No. PCT/US2010/023173, mailed Aug. 25, 2011.
International Search Report and Written Opinion for International Application No. PCT/US2010/023173, dated May 20, 2010, Beatrix Tietze-Epoupa and Frank Mueller.
International Search Report and Written Opinion for International Application No. PCT/US2013/051331, mailed Nov. 27, 2013.
Jama et al., "Direct PCR From Whole Blood," poster 102808 [online] at http://www.kapabiosystems.com/public/files/pdfs (2008).
Johnson et al., "Role of Subunit-9 of Mitochondrial ATP Synthase in Batten Disease," American Journal of Medical Genetics 57:350-360, (1995).
Klepàrnìk et al., "Electromigration Behaviour of DNA Molecules at the Free Electrolyte-Polymer Solution Interface," J. Chromatogr. 772:243-253 (1997).
Kolesar et al, "Direct Quantification of AD-36 Adenovirus DNA by Capillary Electrophoresis with Laser-Induced Fluorescence", J. Chromatography B, pp. 1-8 (2000).
Kraff et al., "Screen for Excess FMR1 Premutation Alleles Among Males with Parkinsonism," Arch. Neurol. 64:1002-1006 (2007).
Kremer et al., "Mapping of DNA instability at the fragile X to a trinucleotide repeat sequence p(CCG)n," Science 252:1711-1714 (1991).
Kunst et al., "FMR1 in Global Populations", Am. J. Hum. Genet. 58: 513-522 (1996).
Kwon, SH. et al. "Molecular screening for fragile X syndrome in mentally handicapped children in Korea" J. Korean Med Sci., vol. 16, pp. 271-275, 2001.
Larsen et al., "Haplotype and AGG-Interspersion Analysis of FMR1 (CGG)n Alleles in the Danish Population: Implications for Multiple Mutational Pathways Towards Fragile X Alleles," Am. J. Med. Genet. 93:99-106 (2000).
Latham et al., "Evaluation of a Novel FMR1 PCR Assay that Can Amplify Fragile X Full Mutations," abstract published at http://submissions.miracd.com/acmg (Mar. 25, 2009).
Levinson et al., "Improved Sizing of Fragile X CCG Repeats by Nested Polymerase Chain Reaction," Am. J. Med. Genet. 51:527-534 (1994).

(56) References Cited

OTHER PUBLICATIONS

Lyon et al., "A Rapid PCR Assay Suitable for Fragile X Population Screening," abstract posted on http://submissions.miracd.com/acmg on or before Mar. 19, 2009.
McPherson, M. J. & S. G. Moller, PCR: The Basics (2nd Ed., Taylor & Francis) (2006), Chapter 3, pp, 23-63, Chapter 4, pp. 65-85, Chapter 7, pp. 137-183, Chapter 11, pp. 257-281.
Musso et al., "Betaine, Dimethyl Sulfoxide, and 7-Deaza-dGTP, a Powerful Mixture for Amplification of GC-Rich DNA Sequences," J. Mol. Diagn. 8:544-550 (2006).
Nolin et al., "Expansion of the Fragile X CGG Repeat in Females with Premutation of Intermediate Alleles," Am. J. Hum. Genet. 72:454-464 (2003).
Nygren et al., "Methylation-specific multiplex ligation-dependent probe amplification enables a rapid and reliable distinction between male FMR1 premutation and full-mutation alleles," J. Mol. Diag. 10(6):496-501 (2008).
O'Connell et al., "Standardization of PCR Amplification for Fragile X Trinucleotide Repeat Measurements," Clin. Genet. 61:13-20 (2002).
Oberle et al., "Instability of a 550-base pair DNA segment and abnormal methylation in fragile X syndrome." Science 252:1097-1102 (1991).
Parida, M. et al. Loop mediated isothermal amplification (LAMP): A new generation of innovative gene amplification technique; perspectives in clinical diagnosis of infectious diseases. Rev. Med. Virol., vol. 18 (6), p. 407-421, 2008.
Pembrey et al., "An Assessment of Screening Strategies for Fragile X Syndrome in the UK," Health Technol. Assess. 5:1-95 (2001).
Pergolizzi et al., "Detection of full fragile X mutation," Lancet 339:271-272 (1992).
Ralser et al., "An Efficient and Economic Enhancer Mix for PCR," Biochem. Biophys. Res. Commun. 347, 747-751 (2006).
Saluto et al., "An Enhanced Polymerase Chain Reaction Assay to Detect Pre- and Full Mutation Alleles of the Fragile X Mental Retardation 1 Gene," J. Mol. Diagn. 7:605-612 (2005).
Saul et al., "Fragile X Syndrome Detection in Newborns—Pilot Study," Genet. Med. 10:714-719 (2008).
Schnoor et al., "Characterization of the Synthetic Compatible Solute Homoectoine as a Potent PCR Enhancer," Biochem. Biophys. Res, Commun. 322, 867-872 (2004).
Sermon et al., "PGD in the Lab for Triplet Repeat Diseases—Myotonic Dystrophy, Huntington's Disease and Fragile-X Syndrome," Mol. Cell. Endocrinol. 183:S77-S85 (2001).
Sermon et al., "Preimplantation Diagnosis for Fragile X Syndrome Based on the Detection of the Non-Expanded Paternal and Maternal CGG," Prenat. Diagn. 19:1223-1230 (1999).
Sista et al., "Development of a Digital Microfluidic Platform for Point of Care Testing," Lab Chip 8:2091-2104 (2008).
Snow et al., "Sequence Analysis of the Fragile X Trinucleotide Repeat: Implications for the Origin of the Fragile X Mutation," Hum. Mol. Genet. 3:1543-1551 (1994).
Stewart et al., "Polymerase δ displaces the primer into a flap for processing" J. Biol. Chem. 283: 31356-31365 (2008).
Strien et al., "Enhancement of PCR Amplification of Moderate GC-Containing and Highly GC-Rich DNA Sequences," Mol. Biotechnol. 54:1048-1054 (2013).
Strom et al., "Development of a Novel, Accurate, Automated, Rapid, High-Throughput Technique Suitable for Population-Based Carrier Screening for Fragile X Syndrome," Genetics in Medicine 9:199-207 (2007).

Tassone et al., "A Rapid Polymerase Chain Reaction-Based Screening Method for Identification of All Expanded Alleles of the Fragile X (FMR1) Gene in Newborn and High-Risk Populations," J. Mol. Diagn. 10:43-49 (2008).
Tzeng, CC. et al. "An effective strategy of using molecular testing to screen mentally retarded individuals for fragile X syndrome" Diagnostic Molecular Pathology, vol. 10(1), p. 34-40, 2001.
Vartanian et al., "Hypermutagenic PCR involving all four transitions and a sizeable proportion of transversions," 1996, Nucleic Acids Research, vol. 24, No. 14, 2627-2631, Oxford University Press.
Vasudevamurthy, Madhusudan, "Betaine Analogues and Related Compounds for Biomedial Applications," Department of Chemical and Process Engineering, University of Canterbury, Christchurch, New Zealand (2006).
Verkerk et al., "Identification of a gene (FMR-1) containing a CGG repeat coincident with a breakpoint cluster region exhibiting length variation in fragile X syndrome," Cell 65:905-914 (1991).
Vincent et al., "Abnormal pattern detected in fragile-X patients by pulsed-field gel electrophoresis," Nature 349:624-626 (1991).
Wallace et al., "Fragile X Analysis: A Muiti-Centre Assessment of the Abbott Molecular Fragile X Analyte Specific Reagent (ASR) Kit," Technology Assessment Report—Abbott Molecular Fragile X ASR, National Genetics Reference Laboratory, Manchester, UK, Jan. 2008, pp. 1-105.
Wang et al., "A rapid, non-radioactive screening test for fragile X mutations at the FRAXA and FRAXE loci," Journal of Medical Genetics 32:170-173 (1995).
Warner et al., "A general method for the detection of large CAG repeat expansions by fluorescent PCR," J. Med Genet, 1996, vol. 33, 1022-1026.
Weisman-Shomer et al., "Interruption of the Fragile X Syndrome Expanded Sequence d(CGG)n by Interspersed d(AGG) Trinucleotides Diminishes the Formation and Stability of d(CGG)n Tetrahelical Structures" Nucleic Acids Res. 28:1535-41 (2000).
Wiedmann et al., "Ligase Chain Reaction (LCR)—Overview and Applications," PCR Methods and Applications 3, S51-S64 (1994).
Wilson et al., "Consensus Characterization of 16 FMR1 Reference Materials: A Consortium Study", Journal of Molecular Diagnostics, 10(1): 2-12 (2008).
Wilson et al., "Random Mutagenesis by PCR," Curr. Protoc. Molec. Biol., Ch. 8, Unit 8.3 (2000) pp. 8.3.1-8.3.9.
Yrigollen et al., "The role of AGG interruptions in the transcription of FMR1 premutation alleles," PLOS One, 6(7): e21798 (2011).
Yrigollen et al., "AGG interruptions within the maternal FMR1 gene reduce the risk of offspring with fragile X syndrome," Genet. Med., 14(8): 729-736 (2012).
Yu et al., "Fragile X genotype characterized by an unstable region of DNA," Science 252:1179-1181 (1991).
Zhang et al, "Direct DNA Amplification from Crude Clinical Samples Using a PCR Enhancer Cocktail and Novel Mutants of Taq," J. Mol. Diagn. 12:152-161 (2010).
Zhong et al., "Fragile X 'Gray Zone' Alleles: AGG Patterns, Expansion, Risks, and Associated Haplotypes," Am. J. Med. Genet. 64:261-5 (1996).
Zhong et al., "Fragile X gene instability: anchoring AGGs and linked microsatellites," Am. J. Hum. Genet. 57:351-361 (1995).
Zhou et al., "Simplified Molecular Diagnosis of Fragile X Syndrome by Fluorescent Methylation-Specific PCR and GeneScan Analysis," Clinical Chemistry, 52: 1492-1500 (2006).
Zhou, et al., "Robust Fragile X (CGG)n Genotype Classification Using a Methylation Specific Triple PCR Assay," J. Med. Genet. 41:e45 (2004), downloaded from http://www.jmg.bmj.com on Sep. 5, 2008.

* cited by examiner

COMPREHENSIVE FMR1 GENOTYPING

This application claims the benefit of priority under 35 U.S.C. §119 to U.S. Provisional Application No. 61/674,167, filed on Jul. 20, 2012, which is incorporated herein by reference in its entirety.

Work described in this application was partially funded by the Federal government under National Institute of Child Health and Human Development (NICHD) Grant No. R44HD066953. The government may have certain rights in the invention.

SEQUENCE LISTING

The instant application contains a Sequence Listing which has been submitted in ASCII format via EFS-Web and is hereby incorporated by reference in its entirety. Said ASCII copy, created on Jul. 19, 2013, is named 10256.0039-00000_SL.txt and is 3,625 bytes in size.

The present disclosure relates generally to an apparatus and software for automated nucleic acid analysis, particularly to methods for analyzing and genotyping regions in nucleic acid compositions, such as isolated nucleic acid products, fragments, and templates, that contain nucleotide repeats.

Genetic loci that comprise regions of nucleotide repeats (e.g., dinucleotide repeats, trinucleotide repeats, etc.) are common in the human or animal genome. Genetic loci that have enriched GC content are also common. In some circumstances, the expansion of GC-rich regions, or the expansion of nucleotide repeats, can be associated with various disease states. For example, the expansion of CGG repeats in the 5' untranslated region (UTR) of the Fragile X Mental Retardation-1 gene (FMR1), located on the X chromosome, is associated with Fragile X Syndrome (FXS) and related disorders and phenotypes. In most people, the trinucleotide CGG is repeated approximately 5-44 times in the 5' untranslated region (UTR) of the FMR1 gene ("CGG repeat region"). Expansions in this region to greater than about 45 CGG repeats, and particularly to greater than about 200 CGG repeats, have been associated with FXS. FXS phenotypes may include mental retardation, autism, anxiety, and other cognitive or behavioral conditions. (*J. Mol. Diag.* 10(6): 496-501 (2008)). Likewise, expansion of the CCG trinucleotide repeat region ("CCG repeat region") in the 5' UTR of the FMR2 gene is associated with X-linked intellectual disabilities, and particularly with Fragile X syndrome E (FRAXE). FRAXE is a common form of X-linked mental retardation.

Methods for genotyping GC-rich sequences and sequences comprising nucleotide repeats, such as the CGG and CCG repeats in FMR1 and FMR2, include restriction enzyme digestion and polymerase chain reaction (PCR) strategies. Restriction digest analysis can provide a crude measure of the size of a triplet repeat region. However, restriction digest analysis is limited in resolution, does not easily detect short interruptions (such as single codon AGG interruptions within a CGG repeat region) and cannot determine methylation status.

PCR strategies may provide greater accuracy in reconstructing various genotypes. However, limitations exist in the amplification and sequencing of genetic loci that comprise long repeat sequences or contain GC-rich sequences that hinder the ability to reconstruct genotypes for these loci. Efforts to optimize PCR procedures for the analysis of the CGG repeats in FMR1, for example, have been attempted, and include modifications to conventional PCR assay conditions. (See *Genome Res.* 6(7): 633-8, (1996); *J. Mol. Diag.* 8: 544-550, (2006); and *Am. J. Med. Genet.* 51(4): 527-34, (1994)). More recently, PCR techniques have been developed that permit more reliable amplification of genomic loci having over 200 CGG or CCG repeats. See US Application Nos. 2010/0209970, 2010/0243451, and 2012/0107824, which describe PCR methods for sequencing GC-enriched repeat regions, which are hereby incorporated by reference in their entirety. These methods often provide information characterizing a repeat region, such as the length of the region, the number of repeats within the region, and the presence of any interruptions within the repeat region. However, PCR alone does not permit rapid or high throughput reconstruction of the full genotype from the parameter information characterizing the GC-rich region, especially where the region contains short interruptions, such as the single codon AGG sequences observed in the FMR1 5' UTR.

Recent studies have indicated that AGG interruptions within the CGG repeat region in the 5' UTR of FMR1 may confer DNA stability and may reduce the risk of expansion in the triplet repeat region in offspring that is associated with FXS and related disorders, including Fragile X-associated tremor/ataxia syndrome (FXTAS), fragile X-related primary ovarian insufficiency (FXPOI), and dopamine-responsive Parkinsonism. (See Eichler et al., *Nat. Genet.* 8: 88-94 (1994); Nolin et al., *Am. J. Hum. Genet.* 72: 454-64 (2003); Yrigollen et al., Genet. Med., in press). Although it is possible to reconstruct genotypes, such as the CGG repeat region in the 5' UTR of FMR1, using manual interpretation, this process can be complex and time-consuming. Thus, a method for fast, accurate, and high-throughput genotyping of regions having nucleotide repeats or high GC content, such as the CGG repeat region in the 5' UTR of FMR1 and the CCG repeat region in the 5' UTR of FMR2, could offer diagnostic benefits. For example, automation of data interpretation could improve workflow in the diagnostics laboratory by allowing for faster validation of assay data and by ensuring robust and accurate sequencing results.

Accordingly, disclosed herein are methods for the automated reconstruction of a genotype comprising one or more GC-rich region or one or more nucleotide repeat region.

In various embodiments, a method is disclosed for the automated reconstruction of a genotype, comprising (a) providing a sample from a patient, wherein the sample comprises a nucleic acid having at least one repeat or GC-rich region; (b) determining parameter information for the nucleic acid; and (c) using an apparatus to apply automated exhaustive enumeration to the parameter information to generate a reconstructed genotype. In some embodiments, determining the parameter information comprises determining a total length of the at least one repeat or GC-rich region, a distance in the forward direction to any interruptions in the region, and a distance in the reverse direction to any interruptions in the region. In some embodiments, exhaustive enumeration comprises (a) using the total length of the at least one repeat or GC-rich region and either the distance in the forward direction to any interruptions in the region or the distance in the reverse direction to any interruptions in the region to generate a set of potential genotypes comprising all possible arrangements of the interruptions in the region; and (b) evaluating the set of potential genotypes to determine a solution genotype that satisfies all the parameter information. In certain embodiments, the apparatus used to conduct automated exhaustive enumeration comprises a processor and a memory device communicatively coupled to the processor, wherein the memory device has stored therein machine-executable instructions that, when executed by the processor, cause the processor to receive parameter information and to conduct an exhaustive enumeration analysis. In some embodiments, the reconstructed genotype can be confirmed by manually comparing the genotype to the parameter information, by performing a restriction digest, or by sequencing the nucleic acid having at least one repeat or GC-rich region.

In various embodiments, the methods described above can be used to reconstruct a genotype when a genotype from a parent of the patient is not known In various embodiments, the methods described above can be used to reconstruct a genotype for the FMR1 or FMR2 genes or fragments thereof, or the CGG and CCG repeat regions of those genes and fragments. In these embodiments, determining the parameter information comprises determining a total length of at least one CGG or CCG repeat region, a distance in the forward direction from a specified position to any AGG interruptions in the repeat region, and a distance in the reverse direction from a specified position to any AGG interruptions in the repeat region. In some embodiments, the parameter information is determined by polymerase chain reaction and capillary electrophoresis.

In certain embodiments, the methods described above can be used to detect a genotype or phenotype associated with an FMR1 or FMR2 disorder. In some embodiments, the FMR1 or FMR2 disorder is Fragile X Syndrome (FXS), Fragile X syndrome E (FRAXE), Fragile X-associated tremor/ataxia syndrome (FXTAS), fragile X-related primary ovarian insufficiency (FXPOI), or dopamine-responsive Parkinsonism.

In various embodiments, an apparatus is provided for the automated reconstruction of a genotype, comprising (a) a processor; and (b) a memory device communicatively coupled to the processor, the memory device having stored therein machine-executable instructions that, when executed by the processor, cause the processor to (i) receive parameter information comprising the total length of at least one repeat or GC-rich region, the distance in the forward direction to any interruptions in the region, and the distance in the reverse direction to any interruptions in the region; (ii) generate a set of potential genotypes comprising all possible arrangements of the interruptions in the repeat or GC-rich region; (iii) evaluate the set of potential genotypes to produce a solution genotype that satisfies all the parameter information; and (iv) store the solution genotype on the memory device. In some embodiments, the apparatus further comprises a monitor communicatively coupled to the processor and memory device, wherein the machine-executable instructions stored on the memory device instruct the processor to display the solution genotype on the monitor. In some embodiments, the apparatus further comprises a printer communicatively coupled to the processor and memory device, wherein the machine-executable instructions stored on the memory device instruct the processor to print the solution genotype on the printer.

In various embodiments, a machine-readable medium is provided, comprising machine-executable instructions that, when executed by a processor, causes the processor to (a) receive parameter information comprising the total length of at least one repeat or GC-rich region, the distance in the forward direction to any interruptions in the region, and the distance in the reverse direction to any interruptions in the region; (b) generate a set of potential genotypes comprising all possible arrangements of the interruptions in the repeat or GC-rich region; (c) evaluate the set of potential genotypes to produce a solution genotype that satisfies all the parameter information; and (d) store the solution genotype on a memory device. In some embodiments, the machine-executable instructions instruct the processor to display the solution genotype on a monitor. In some embodiments, the machine-executable instructions instruct the processor to print the solution genotype on a printer.

DESCRIPTION OF CERTAIN EXEMPLARY EMBODIMENTS

Reference will now be made in detail to certain exemplary embodiments according to the present disclosure, certain examples of which are illustrated in the accompanying drawings.

The section headings used herein are for organizational purposes only and are not to be construed as limiting the subject matter described. All documents, or portions of documents, cited in this application, including but not limited to patents, patent applications, articles, books, and treatises, are hereby expressly incorporated by reference in their entirety for any purpose. To the extent publications and patents or patent applications incorporated by reference contradict the invention contained in the specification, the specification will supersede any contradictory material.

To assist in understanding the present invention, certain terms are first defined. Additional definitions are provided throughout the application.

In this application, the use of the singular includes the plural unless specifically stated otherwise. Also in this application, the use of "or" means "and/or" unless stated otherwise. Furthermore, the use of the term "including," as well as other forms, such as "includes" and "included," are not limiting. Any range described herein will be understood to include the endpoints and all values between the endpoints.

As used herein, a "nucleic acid" is any contiguous nucleobase residues or analogs that have been isolated from a subject and/or for which a genotype reconstruction is sought. A nucleic acid can comprise a gene, gene fragment, or genomic region isolated from a subject. As used herein, a "genotype" is the nucleobase sequence of a nucleic acid.

As used herein, "GC-richness" is the fraction or percentage of total nucleobase residues in a nucleic acid or a fragment of that nucleic acid that are guanine residues, cytosine residues, or analogs thereof. For example, a 100 nucleotide sequence that contains exactly 30 cytosines, exactly 30 guanines, exactly one cytosine analog, and exactly one guanine analog has a GC-richness of 62%. In some embodiments, a "GC-rich" nucleic acid or region of a nucleic acid is one that contains more than about 50% guanine residues, cytosine residues, or analogs thereof (e.g., more than about 50, 51, 55, 60, 65, 70, 75, 80, 85, 90, 95, 96, 97, 98, 99, or 99.5% guanine residues, cytosine residues, or analogs thereof, or any percentage in between).

As used herein, a "repeat" or "nucleotide repeat" refers to a nucleic acid or a region of a nucleic acid comprising any short sequence of 1-20 nucleobase residues in length (e.g., a dinucleotide, trinucleotide, tetranucleotide, pentanucleotide, hexanucleotide sequence, etc.) wherein the short sequence is repeated 2 or more times (e.g., 2, 3, 4, 5, 10, 15, 20, 50, 100, 200, 500, or more repeats). For example, a nucleotide repeat would encompass a region of a nucleic acid in which the short sequence CGG is repeated two or more times. A nucleic acid or a region of a nucleic acid can be both a repeat and GC rich region. For example, the nucleic acid or region of a nucleic acid can comprise di-, tri-, tetra-, penta- or hexa-nucleotide repeats of guanine residues, cytosine residues, or analogs thereof.

A nucleic acid can comprise one or more nucleotide repeats or GC-rich regions that contain one or more interruptions. As used herein, an "interruption" in a nucleic acid refers to the presence of one or more nucleobase residues or analogs in the nucleic acid that are inconsistent with the repeat pattern or, in a GC-rich region, comprise a nucleobase other than G or C (or analogs thereof). For example, a GC-rich, nucleotide repeat region could encompass a sequence comprising 40 CGG trinucleotide repeats with two AGG sequences interspersed within the 40 CGG repeats.

FMR1 is a gene on the X chromosome that encodes the fragile X mental retardation protein (FMRP). This protein, most commonly found in the brain, is essential for normal cognitive development and female reproductive function. The 5' untranslated region (5' UTR) of the FMR1 gene can comprise one or more regions (e.g., 1, 2, 3, 4, 5, or more regions) having CGG repeats. The presence of a region comprising 40 or more CGG repeats in the 5' UTR is thought to be associated with FMR1-related disorders. The 5' UTR of the FMR1 gene can also comprise one or more AGG sequences that interrupt a CGG repeat region.

FMR2 is a gene on the X chromosome that encodes the fragile mental retardation 2 protein. The 5' UTR of the FMR2 gene can comprise one or more regions (e.g., 1, 2, 3, 4, 5, or more regions) having CCG repeats. Expansion of a CCG repeat region has been associated with X-linked intellectual disabilities, and particularly with Fragile X syndrome E (FRAXE). FRAXE is a common form of X-linked mental retardation.

I. Comprehensive Genotyping

Disclosed herein are methods for the automated reconstruction of a genotype comprising one or more nucleotide repeat regions or GC-rich regions. For example, the methods disclosed herein can be used to reconstruct a genotype from a nucleic acid or fragment thereof comprising CGG repeats and interspersed AGG interruptions, or to reconstruct a genotype comprising CCG repeats. In some embodiments, the methods can be used to reconstruct the repeat region of the FMR1 or FMR2 gene, or fragments thereof, or the 5' UTR of FMR1 or FMR2, or fragments thereof, isolated from a subject. In certain embodiments, the methods disclosed herein are used to assist in reconstructing the genotype of FMR1, including the CGG repeat pattern and the location and organization of AGG interruptions within the 5' UTR of FMR1. In other embodiments, the methods disclosed herein are used to assist in reconstructing the genotype of FMR2, including the CCG repeat pattern.

In some embodiments, the methods disclosed herein are used to determine the genotype of a nucleic acid or fragment thereof from a patient sample, wherein the nucleic acid has at least one repeat or GC-rich region, and wherein the related genotype from at least one of the parents of the patient is not known. In certain embodiments, the methods disclosed herein are used to determine a genotype for the CGG or CCG repeat region in FMR1 or FMR2 from a patient sample, wherein the related FMR1 or FMR2 genotype from at least one of the parents of the patient is not known.

In various embodiments, a method for the automated reconstruction of a genotype comprises providing a sample from a patient, wherein the sample contains a nucleic acid or fragment thereof having one or more repeat regions or GC-rich regions. In some embodiments, information characterizing the nucleic acid (i.e., "parameter information") is collected, such as the total length of the repeat or GC-rich region and the distance in the forward and reverse directions to any interruptions in the repeat or GC-rich region. In some embodiments, the collected information is automatically analyzed using exhaustive enumeration, using an apparatus comprising a processor programmed to conduct an automated exhaustive enumeration analysis. In some embodiments, the exhaustive enumeration reconstructs a solution genotype (i.e., a genotype that satisfies all of the parameter information). In certain embodiments, the accuracy of the solution genotype can be evaluated by manually analyzing the genotype to confirm that it comports with all of the parameter information, or by conducting any other confirmatory assay (e.g., restriction enzyme digest, Sanger sequencing, or other forms of high throughput sequencing). In some embodiments, the solution genotype can be displayed or stored electronically on a computer, or can be printed for subsequent diagnostic and therapeutic purposes.

In certain embodiments, the reconstructed genotype can be used to detect a mutation or genotype, or to diagnose or assist in diagnosing a disorder associated with a mutation in a repeat region or GC-rich region, such as an FMR1 or FMR2 related mutation, genotype, or disorder.

In various embodiments, parameter information characterizing a nucleic acid can be obtained using any suitable method, such as PCR or restriction digest analyses. In certain embodiments, the parameter information includes the overall length of the repeat or GC-rich region, as well as the distance from the start of the repeat or GC-rich region to a first or subsequent interruption in the forward direction and in the reverse direction. In some embodiments, an apparatus is provided, comprising a processor programmed to analyze parameter information and to reconstruct a genotype from the information. In certain embodiments, the apparatus is used to reconstruct the genotype of the nucleic acid from the information characterizing the nucleic acid. In some embodiments, the apparatus uses exhaustive enumeration to evaluate all possible genotype reconstructions based on the length of the repeat or GC-rich region and the interruptions in the forward or reverse direction to select the reconstruction that satisfies all the parameter information (e.g., the genotype that places the interruptions in the correct positions in both the forward and reverse directions). In certain embodiments, the apparatus provides a report of the reconstructed genotype that can be displayed on a screen, saved digitally for future use, or printed as a paper record.

In various embodiments, parameter information regarding a nucleic acid can be obtained using any method known in the art, so long as it includes information regarding the total length of a repeat or GC-rich region in the nucleic acid and the distance from the start ("forward direction") and end ("reverse direction") of the GC-rich region to any interruptions. In some embodiments, restriction enzymes that cleave a nucleic acid site-specifically can be used to analyze a repeat or GC-rich region and thereby generate parameter information. For example, the presence of AGG interruptions within a CGG repeat tract of FMR1 can be detected by digesting a nucleic acid with the restriction enzyme Eicl (New England Biolabs Inc., Ipswich, Mass., USA). In other embodiments, PCR methods can be used to generate the necessary information. For example, restriction digest and/or PCR methods can be used with an FMR1 or FMR2 gene or fragments thereof isolated from a patient in order to determine the length of one or more CGG or CCG repeats. The methods can also be used to determine the distance in the forward and reverse directions from the first and last CGG or CCG triplets to any internal interruptions, such as AGG interruptions interspersed within a CGG repeat region in the FMR1 gene.

In some embodiments, suitable methods for generating parameter information include polymerase chain reaction (PCR), real-time PCR (RT-PCR), nucleic acid sequence-base amplification (NASBA), ligase chain reaction, multiplex ligatable probe amplification, invader technology (Third Wave), rolling circle amplification, in vitro transcription, strand displacement amplification, transcription-mediated amplification (TMA), RNA (e.g., Eberwine) amplification, loop-mediated isothermal amplification, or any other methods that are known to one of skill in the art. For example, FMR1 parameter information can be generated using a two-tier PCR approach with a CGG linker primer and the Human FMR1 PCR kit (Asuragen Inc., Austin, Tex., USA). See Tassone et al., *J Mol Diagn.* 10(1):43-49 (2008); Chen et al., *J Mol Diagn.* 12(5): 589-600 (2010); Yrigollen et al., *PLoS One* 6(7): e21728 (2011). For example, a nucleic acid comprising at least one GC-rich region can be analyzed by (a) providing at least two PCR primers, including a first primer comprising CGG, CCG, GCG, CGC, GCC, or GGC repeats, and a second primer that anneals to a position outside of the GC-rich region; (b) performing PCR on the nucleic acid with the at least two different primers, wherein the PCR produces a set of PCR products; (c) resolving the set of PCR products with a high resolution technique (such as capillary electrophoresis) to generate a representation of PCR product size and abundance; and (d) deriving from the PCR product size and abundance information the length of the GC-rich region and whether or where within the GC-rich region an interruption is located.

In various embodiments, PCR-amplified nucleic acids are analyzed to generate parameter information, for example using capillary electrophoresis (CE) instruments familiar to those skilled in the art, such as ABI model 3100, 3130, 3730, or 3500 CE instruments (Applied Biosystems, Carlsbad, Calif.). Other implementations, include any instrument capable of electrophoretically or otherwise sizing and/or sequencing an amplified nucleic acid, can also be used. Exemplary PCR and analysis methods for use with repeat or GC-rich regions, such as the CGG and CCG repeat loci in the 5' UTRs of FMR1 and FMR2, are described in US Application Nos. 2010/0209970, 2010/0243451, and 2012/0107824, which are hereby incorporated by reference in their entirety. Any other method of collecting parameter information can also be used (e.g., Sanger sequencing or other forms of high throughput sequencing).

For example, parameter information characterizing the CGG and CCG repeat loci in the 5' UTRs of FMR1 and FMR2 or fragments thereof can be generated using the methods described in U.S. Patent Application No. 2010/0243451, including the primers, polymerase, reagents, and reaction conditions disclosed at paragraphs [0040]-[0051], [0056]-[0060], [0065]-[0067], [0089], [0094], and [0104], which are hereby incorporated by reference.

Once the parameter information characterizing a repeat or GC-rich region has been collected, it is theoretically possible to assemble a genotype using manual interpretation. However, this manual interpretation can be a slow and complex process, particularly when the gene of interest comprises more than one repeat or GC-rich region and/or more than one interruption. For example, an FMR1 gene or fragment thereof comprising two CGG repeat regions and two AGG interruptions would require the evaluation of sixteen potential solutions before the correct genotype could be identified (see below for an explanation of the sixteen possible combinations). Accordingly, in various embodiments, a method for automated genotype reconstruction using exhaustive enumeration is provided. In some embodiments, the use of exhaustive enumeration increases the accuracy and/or speed of genotype reconstruction.

In various embodiments, exhaustive enumeration comprises: (a) providing parameter information regarding the length of one or more repeat or GC-rich regions in a nucleic acid and the number of interruptions within those regions, (b) using the information regarding the length of a repeat or GC-rich region and the distance from the start of the region to each interruption (in either the forward or reverse direction) to generate a set of potential genotypes comprising all possible arrangements of the interruptions, and (c) evaluating the set of potential genotypes to determine the solution genotype that satisfies all the parameter information. In the embodiments where the interruptions in the forward direction are used to construct the possible genotypes, each potential genotype in the set is then evaluated using the information regarding the interruptions in the reverse direction. In the embodiments where the interruptions in the reverse direction are used to construct the possible genotypes, each potential genotype in the set is then evaluated using the information regarding the interruptions in the forward direction. In certain embodiments, the potential genotype that matches the forward and reverse interruption information is selected as the solution genotype.

In an embodiment, the exhaustive enumeration analysis can be represented by formula, $\pi|C_i|$, which indicates the product of the number of potential genotypes for the possible alleles, where $|C_i|$ is the number of candidate genotypes for allele i. As a result, this formula provides the number of possible genotypes that can be reconstructed from the parameter information (i.e., the set of potential genotypes that can be recreated using the length of the repeat or GC-rich region and the number of interruptions within the region in either the forward or reverse directions). In an embodiment, each of the $C_i$ potential genotypes generated using the forward interruption information is individually evaluated using the reverse interruption information to select a solution genotype. In another embodiment, each of the $C_i$ potential genotypes generated using the reverse interruption information is individually evaluated using the forward interruption information to select a solution genotype.

The exhaustive enumeration method can be conducted using an apparatus comprising a processor (e.g., a computer) programmed to conduct exhaustive enumeration analysis. In some embodiments, the processor is programmed to receive information regarding a nucleic acid and then apply exhaustive enumeration to reconstruct a solution genotype for the nucleic acid. In some embodiments, the apparatus also comprises a monitor to display input information and/or the solution genotype. In some embodiments, the solution genotype is stored electronically on the apparatus, and/or is capable of being printed for further diagnostic or therapeutic uses.

As described in more detail in the examples below, the exhaustive enumeration method can be used, in some embodiments, to reconstruct a genotype of the CGG repeat region in the FMR1 gene. The 5' UTR of FMR1 can comprise one or more CGG repeat regions, each of which may contain one or more AGG interruptions within the region. Where more than one AGG interruption is present, these generally do not occur contiguously (i.e., it is rare to find a CGG repeat region comprising $(AGG)_n$, where n is greater than or equal to 2). Various techniques for analyzing the FMR1 gene or fragments thereof, such as the PCR methods described in US Application Nos. 2010/0209970, 2010/0243451, and 2012/0107824, often yield parameter information regarding the length of the CGG repeat region and the distance in the forward and reverse directions to each AGG interruption within the CGG repeat region. In various embodiments, this FMR1 parameter information can be used to generate a list of all potential genotypes having the correct CGG repeat length and the correct AGG interruptions in either the forward or reverse direction. Using exhaustive enumeration, each potential solution can then be evaluated for consistency in the forward and reverse directions, and a solution genotype displaying the correct position(s) for the AGG interruption(s) within the CGG repeat sequence can be selected that satisfies both the forward and reverse distance requirements, and also does not place any AGG interruption proximal to another AGG interruption.

In some embodiments, once a solution genotype is identified using exhaustive enumeration, the solution can be further evaluated by manual comparison to confirm that it satisfies all of the parameter information characterizing the nucleic acid (such as the total length of the repeat or GC-rich region and the distance in the forward and reverse directions to any interruptions), or by conducting any other confirmatory assay known to one of skill in the art (e.g., restriction enzyme digest, Sanger sequencing, or high throughput sequencing). For example, the presence of AGG interruptions within a CGG repeat tract of FMR1 can be confirmed by digesting the nucleic acid sample with the restriction enzyme Ecil (New England Biolabs Inc., Ipswich, Mass., USA).

II. Samples

The methods provided herein relate to the genotyping of a nucleic acid in a sample. In various embodiments, a sample is obtained from a human or non-human animal. For example, the sample may be a patient sample. A "patient sample" is any biological specimen from a patient. The term sample includes, but is not limited to, biological fluids such as blood, serum, plasma, urine, cerebrospinal fluid, tears, saliva, lymph, dialysis fluid, lavage fluid, semen, and/or other liquid samples, as well as cells and tissues of biological origin. Cells and tissues may include buccal cells, mouthwash collections, or skin cells, including hair follicles. The term also includes cells isolated from a human or cells derived therefrom, including cells in culture, cell supernatants, and cell lysates. It further includes organ or tissue culture-derived fluids, tissue biopsy samples, tumor biopsy samples, stool samples, and fluids extracted from physiological tissues, as well as cells dissociated from solid tissues, tissue sections, and cell lysates. It may also include post-mortem solid tissue samples, such as those from brain. The term sample also includes any other cellular or non-cellular specimen obtained from a human or non-human animal that comprises a nucleic acid of interest. In some embodiments, the sample contains less than about 80, 100, 150, 200, 500, 1,000, 1,500, 2,000, 2,500, 3,000, 4,000, or 5,000 ng of the nucleic acid of interest.

In some instances, the sample includes one or more nucleic acids of interest. The nucleic acid of interest can be genomic DNA. The genomic DNA or other nucleic acid of interest may be separated from other DNA and non-DNA components of the sample before being subjected to the methods of the invention. Many methods of DNA purification and separation are known in the art and may be used with the disclosed methods.

In some embodiments, the nucleic acid of interest in the sample may comprise the FMR1 and/or FMR2 genes or fragments thereof, or at least part of the 5' UTR of FMR1 and/or FMR2 (e.g., a portion that comprises the CGG repeats of the 5' UTR of FMR1 or the CCG repeats in the 5' UTR of FMR2). In certain embodiments, the size of the nucleic acid may be about 50, 100, 200, 300, 500, or 700 bp, or 1, 1.5, 2, 2.5, 3, 4, 5, 7, or 10 kb, or any value in between. In some embodiments, the size of the nucleic acid may be between 50 bp and 10 kb, 100 bp and 10 kb, 200 bp and 10 kb, 300 bp and 10 kb, 500 bp and 10 kb, 700 bp and 10 kb, 1 kb and 10 kb, 1.5 bp and 10 kb, 2 bp and 10 kb, 3 bp and 10 kb, 50 bp and 7 kb, 50 bp and 5 kb, 50 bp and 4 kb, 50 bp and 3 kb, 50 bp and 2 kb, 50 bp and 1.5 kb, 100 bp and 7 kb, 200 bp and 5 kb, or 300 bp and 4 kb.

III. Genotyping Apparatus and Machine-Readable Medium

In various embodiments, an apparatus is disclosed for use in the automated reconstruction of a genotype. In some embodiments, the apparatus comprises a processor communicatively coupled to a memory device. In some embodiments, machine-executable instructions are stored on the memory device that, when executed by the processor, cause the processor to conduct exhaustive enumeration analysis. In certain embodiments, the machine-executable instructions cause the processor to (a) accept the input of parameter information regarding the total length of a repeat or GC-rich region, the distance in the forward direction to any interruptions in the region, and the distance in the reverse direction to any interruptions in the region; (b) generate a set of potential genotypes comprising all possible arrangements of the interruptions in the repeat or GC-rich region; (c) evaluate the set of potential genotypes to produce a solution genotype that satisfies all the parameter information; and (d) store the solution genotype on the memory device or on any other memory device that is communicatively coupled to the processor. In certain embodiments, the apparatus further comprises a monitor communicatively coupled to the processor and memory device, wherein the machine-executable instructions stored on the memory device instruct the processor to display the solution genotype on the monitor. In some embodiments, the apparatus further comprising a printer communicatively coupled to the processor and memory device, wherein the machine-executable instructions stored on the memory device instruct the processor to print the solution genotype on the printer.

In various embodiments, the apparatus used to reconstruct a genotype is capable of accepting the input of parameter information regarding a nucleic acid (e.g., the length of any repeat or GC-rich regions and the distance from the start of the regions to each interruption in either the forward or reverse direction). In some embodiments, the apparatus is programmed to use the parameter information to reconstruct the genotype of the nucleic acid using exhaustive enumeration. The apparatus can be programmed to display and/or archive the reconstructed genotype. In some embodiments, the apparatus comprises a means for displaying and/or archiving the reconstructed genotype.

In various embodiments, an apparatus disclosed herein comprises a processor and memory device, wherein the memory device contains machine-readable instructions that instruct the processor to accept the input of parameter information regarding a nucleic acid and conduct exhaustive enumeration analysis, which can be represented by the formula $\pi |C_i|$, which indicates the product of the number of potential genotypes for the possible alleles, where $|C_i|$ is the number of candidate genotypes for allele i. As a result, this formula provides the number of possible genotypes that can be reconstructed from the parameter information (i.e., the set of potential genotypes that can be recreated using the length of the repeat or GC-rich region and the number of interruptions within the region in either the forward or reverse directions). In an embodiment, machine-readable instructions instruct the processor to generate a list of $C_i$ potential genotypes using the forward or reverse interruption information and then individually evaluate each potential genotype against the full set of parameter information to identify a solution genotype. In some embodiments, the apparatus further comprises a means to display the solution genotype (e.g., a monitor to display the genotype visually, a data storage medium to save the genotype in a digital format, and/or a connection for transmitting the solution genotype to a printer or other electronic storage or display device).

In some embodiments, the apparatus is a computer, wherein the computer comprises a processor and a memory device having computer code stored on it, wherein the computer code instructs the processor to accept the input of parameter information regarding a nucleic acid and then apply exhaustive enumeration to reconstruct a genotype for the nucleic acid. In some embodiments, the computer also comprises a monitor to display input information and/or the reconstructed genotype. In some embodiments, the reconstructed genotype is stored electronically on the computer and/or is capable of being printed for further diagnostic or therapeutic uses. In various embodiments, the computer comprises a device to allow for user interaction. For example, the computer may comprise a keyboard and/or pointing device (e.g., a mouse or a trackball) that allows a user (such as a patient, doctor, or other healthcare worker) to enter parameter information and/or to access and manipulate the reconstructed genotype.

In various embodiments, the instructions to conduct exhaustive enumeration may be stored on an apparatus in a machine-readable medium (e.g., machine-executable instructions, software, computer code, computer programs, etc.). For example, the machine-readable medium can comprise computer code stored in C++, JAVA, PERL, or any other suitable format for computer code. The machine-readable medium can provide instructions to the apparatus for conducting exhaustive enumeration using parameter information regarding a nucleic acid. In various embodiments, the instructions on the machine-readable medium can instruct an apparatus to (a) receive parameter information regarding the total length of a repeat or GC-rich region, the distance in the forward direction to any interruptions in the region, and the distance in the reverse direction to any interruptions in the region; (b) generate a set of potential genotypes comprising all possible arrangements of the interruptions in the repeat or GC-rich region; (c) evaluate the set of potential genotypes to produce a solution genotype that satisfies all the parameter information; and (d) store the solution genotype on a memory device. In some embodiments, the instructions on the machine-readable medium instruct the apparatus to display the solution genotype on a monitor. In some embodiments, the instructions on the machine-readable medium instruct the apparatus to print the solution genotype on a printer.

The instructions stored on a machine-readable medium can be any codes, symbols, or other signals that provide instructions, information, and/or data that can be used by an apparatus (e.g., by a processor in a computer). In some embodiments, the instructions stored on the machine-readable medium encode a program that instructs the apparatus to receive parameter information regarding a nucleic acid, conduct exhaustive enumeration analysis, and store or transmit a reconstructed genotype for the nucleic acid.

In some embodiments, the instructions stored on the machine-readable medium instruct the apparatus to execute an exhaustive enumeration analysis program, which can be represented by the formula $\pi |C_i|$, which indicates the product of the number of potential genotypes for the possible alleles, where $|C_i|$ is the number of candidate genotypes for allele i. As a result, this formula provides the number of possible genotypes that can be reconstructed from the parameter information (i.e., the set of potential genotypes that can be recreated using the length of the repeat or GC-rich region and the number of interruptions within the region in either the forward or reverse directions). In an embodiment, the program generates a list of $C_i$ potential genotypes using the forward or reverse interruption information and then individually evaluates each potential genotype against the full set of parameter information to identify a solution genotype. In some embodiments, the program includes instructions to display and/or archive the reconstructed solution genotype (e.g., to display the genotype on a monitor, to save the genotype to a data storage medium, and/or to transmit the solution genotype to a printer or other electronic storage or display device).

In some embodiments, the instructions stored on the machine-readable medium further encode a user interface that provides a graphical display on a monitor. In some embodiments, the interface allows a user to enter parameter information regarding a nucleic acid (e.g., by allowing the user to upload a data file or by allowing the user to enter information into display fields shown on the user interface). In some embodiments, the user interface provides the user with options for analyzing the parameter information, such as various methods for displaying and/or saving the input data and/or reconstructed genotypes (e.g., by displaying the data on the user's monitor, sending the data to a specified electronic device or electronic address, printing, and/or saving the data to a particular location).

In various embodiments, a reconstructed genotype can be stored as data in a storage medium physically connected to the apparatus (e.g., on an internal memory device such as a hard drive on a computer) and/or stored on a remote storage device that is communicatively connected to the apparatus (e.g., by a wired or wireless intranet or internet connection and the like). In some embodiments, the user interface provides the user with options for automatically storing the reconstructed genotype in a particular location, printing the genotype, and/or sending the genotype to a specified electronic device or electronic address (e.g., to the email address of the medical professional that requested the genotype reconstruction).

IV. Methods of use

In various embodiments, methods to detect a mutation or genotype comprising a GC-rich or repeat region, or to diagnose or treat a genetic disorder associated with a GC-rich or repeat region are provided, comprising (1) obtaining a sample from a patient; (2) isolating a nucleic acid from the sample that has one or more repeat or GC-rich regions, such as a region comprising CGG or CCG repeats; (3) collecting parameter information from the isolated nucleic acid; (4) entering the sequence information into an apparatus programmed to use exhaustive enumeration to reconstruct a genotype from the parameter information; and (5) using the reconstructed genotype to detect a mutation or genotype or to diagnose a genetic disorder associated with a mutation in a repeat or GC-rich region and/or predict the risk of a genetic disorder in patient or an offspring of the patient and/or make a suitable treatment decision based on the reconstructed genotype. For example, the method can comprise isolating an FMR1 or FMR2 nucleic acid or fragments thereof from a patient sample, determining parameter information for the FMR1 or FMR2 nucleic acid, applying exhaustive enumeration to the parameter information to generate a reconstructed genotype for the repeat region in FMR1 or FMR2, and using the reconstructed genotype to detect a mutation or genotype associated with an FMR1 or FMR2 genetic disorder, or to diagnose and/or predict the risk of and/or make treatment decisions regarding an associated disorder.

Numerous genes and genomic regions comprise repeat or GC-rich regions and are associated with genetic disorders, making them potential diagnostic and therapeutic targets. Accordingly, in various embodiments the exhaustive enumeration methods disclosed herein can be used to reconstruct genotypes for these genetic loci and can be used to diagnose, prognose, and/or guide treatment decisions for the associated genetic disorders. In some embodiments, the exhaustive enumeration methods disclosed herein can be used to reconstruct a genotype for the repeat region(s) of the FMR1 or FMR2 genes. In some embodiment, these reconstructed genotypes can assist in the diagnosis of FXS, FRAXE, FXTAS, FXPOI, and dopamine-responsive Parkinsonism, which are associated with the length of CGG repeat regions in the 5' UTR of FMR1 and CCG repeat regions in the 5' UTR of FMR2. For example, a reconstructed FMR1 genotype having greater than about 45 CGG repeats, and particularly a genotype having greater than about 200 CGG repeats, in the 5' UTR can be used to diagnose FXS and associated disorders.

In further embodiments, the exhaustive enumeration methods may be used to detect genotypes associated with other disorders of repeat or GC-rich regions, such as spinocerebellar ataxia type 1, spinocerebellar ataxia type 2, spinocerebellar ataxia type 3, spinocerebellar ataxia type 6, spinocerebellar ataxia type 7, spinocerebellar ataxia type 8, Friedrich's ataxia, progressive myoclomus epilepsy, amyotrophic lateral sclerosis, myotonic dystrophy, Huntington's disease, spinobulbar muscular atrophy, Dentatorubropallidoluysian atrophy, and/or spinocerebellar ataxia. Genetic loci associated with these conditions are known in the art and include, without limitation, SCA1, SCA2, SCA3, CACNA1A, SCA7, SCA8, X25, CSTB, C9ORF72, DMPK, ZNF9, HTT, AR, ATN1, ATXN1-3, ATXN7, ATXN10, CACNA1A, SCA8, PPP2R2B, and TBP. See, e.g., *Nat Genet.* 1996 May; 13(1): 105-8; *Nat Genet.* 1996 May; 13(1):109-13. Hyperexpansion and/or hypermethylation of the GC-rich and/or repeat regions at these loci are associated with the diseases. Table 6 shows examples of genetic loci that can be used with the exhaustive enumeration methods disclosed herein, and the relationship between GC-rich and/or repeat regions in those loci and disease genotypes or phenotypes.

For example, exhaustive enumeration can be used with to detect genotypes associated with disorders of SCA1 or SCA2, such as Spinocerebelllar ataxia types 1 and 2, which are associated with expansion of their CAG repeat regions. For example, parameter information can be provided regarding the total length of one or more CAG repeats in the SCA1 or SCA2 genes, as well as the distance in the forward and reverse directions to the CAT or CAA interruptions in the CAG repeats. Exhaustive enumeration, using the total length of the one or more CAG repeats and either the distance in the forward or reverse direction to any interruptions, can be applied to generate a set of potential genotypes for the SCA1 or SCA2 gene. The potential genotypes can be evaluated to determine a solution genotype that satisfies all the parameter information. The identified solution genotype can be used to detect a mutation or a genotype, or to diagnose or assist in diagnosing, an SCA1 or SCA2 related mutation, genotype, or disorder.

EXAMPLES

The following examples serve to illustrate, and in no way limit, the present disclosure.

Example 1

Exhaustive Enumeration of a CGG Locus in FMR1

Standard PCR and capillary electrophoresis (CE) analysis of the FMR1 gene may provide parameter information characterizing a CGG repeat locus, such as: (1) the overall length of the CGG repeat locus, (2) Anchored A ("Anch A") mapping, and (3) Anchored T ("Anch T") mapping. The overall length data reveals the total length of the CGG repeat region (including any AGG interruptions). The Anch T data indicates the locations of AGGs within the CGG locus in the forward direction, while the Anch A data indicates the locations of the AGGs in the reverse direction.

TABLE 6

| Disease | Gene | Repeat number Normal | Repeat number Mutant | Repeat position | Repeat variant |
|---|---|---|---|---|---|
| Fragile X syndrome | FMR1 | (CGG) < 45 | (CGG) > 200 | 5'-UTR | AGG |
| Fragile X (FRAXE) mental retardation | FMR2 | (CCG) < 35 | (CCG) > 200 | 5'-UTR | CTG |
| Myotonic dystrophy | DMPK | (CTG) < 35 | (CTG) > 50 | 3'-UTR | CCG, CTC |
| Spinocerebelllar ataxia type 8 | SCA8 | (CTG) < 40 | (CTG) > 110 | Antisense RNA | CCG, CTA, CTC, CCA or CTT |
| Friedrich's ataxia | X25 | (GAA) < 35 | (GAA) > 100 | Intron 1 | GGA, GAG |
| Spinobulbar muscular atrophy | AR | (CAG) < 30 | (CAG) > 40 | Coding | |
| Huntington disease | IT15 | (CAG) < 40 | (CAG) > 40 | Coding | |
| Dentatorubral pallidoluysian atrophy | DRPLA | (CAG) < 35 | (CAG) > 50 | Coding | |
| Spinocerebelllar ataxia type 1 | SCA1 | (CAG) < 40 | (CAG) > 40 | Coding | CAT |
| Spinocerebelllar ataxia type 2 | SCA2 | (CAG) < 30 | (CAG) > 35 | Coding | CAA |
| Spinocerebelllar ataxia type 3 | SCA3 | (CAG) < 40 | (CAG) > 40 | Coding | |
| Spinocerebelllar ataxia type 6 | CACNA1A | (CAG) < 20 | (CAG) > 20 | Coding | |
| Spinocerebelllar ataxia type 7 | SCA7 | (CAG) < 40 | (CAG) > 40 | Coding | normal allele has no interruption |
| Progressive myoclomus epilepsy type | CSTB | ($C_4GC_4GCG$ (SEQ ID NO: 10)) < 3 | ($C_4GC_4GCG$ (SEQ ID NO: 10)) > 50 | Promoter | |

Table 1 shown below is an example of an FMR1 CGG locus having a total repeat length of 23 trinucleotides, with two AGG interruptions. Table 1 shows the position counts in the forward and reverse directions from the start and end of the CGG repeat locus to each of the AGG interruptions.

TABLE 1

| 1 | 2 | 3 | 4 | 5 | 6 | 7 | 8 | 9 | 10 | 11 | 12 |
|---|---|---|---|---|---|---|---|---|----|----|----|
| CGG | CGG | CGG | CGG | AGG | CGG | CGG | CGG | CGG | CGG | CGG | CGG |
| 23 | 22 | 21 | 20 | 19 | 18 | 17 | 16 | 15 | 14 | 13 | 12 |
| 13 | 14 | 15 | 16 | 17 | 18 | 19 | 20 | 21 | 22 | 23 | |
| CGG | CGG | CGG | CGG | CGG | AGG | CGG | CGG | CGG | CGG | CGG | |
| 11 | 10 | 9 | 8 | 7 | 6 | 5 | 4 | 3 | 2 | 1 | |

Table 1 discloses SEQ ID NO: 1.

The CE report for this example would indicate an overall CGG repeat length of {23}, corresponding to the length of the CGG repeat locus. The Anch T assay would report {5,18}, corresponding to the positions of the AGG interruptions within the CGG repeat region, counting in the forward direction. The Anch A assay would report {6,19}, corresponding to the positions of the AGG interruptions when counting in the reverse direction. Given this CE report, the configuration of the CGG repeat locus can be reconstructed relatively easily by using the total CGG length and either the Anch A or Anch T data. The genotype can be written using compact notation as $(CGG)_4(AGG)(CGG)_{12}(AGG)(CGG)_5$ (SEQ ID NO: 1), where the subscripts represent the number of continuous CGG repeats before arriving at an AGG interruption.

While the genotype of an FMR1 gene having a single CGG locus can be manually reconstructed fairly easily, as shown above, the reconstruction task becomes more complex when more than one CGG repeat locus is involved, as shown in the following example.

Example 2

Exhaustive Enumeration of Two CGG Loci in FMR1

It is possible to have more than one CGG repeat locus in an FMR1 gene. For example, an FMR1 gene could have the following two CGG loci:

Locus 1: $(CGG)_{19}(AGG)(CGG)_9$ (SEQ ID NO: 2)

Locus 2: $(CGG)_{10}(AGG)(CGG)_{41}$ (SEQ ID NO: 3)

The complete CE report for this sample is shown in Table 2.

TABLE 2

| CGG_Locus_Length | {29, 52} |
|---|---|
| Anch_T | {11, 20} |
| Anch_A | {10, 42} |

Merely using the information shown in Table 2, it is not a simple task to reconstruct the FMR1 genotype. In particular, it is not clear which components of the Anch T report (or the Anch A report) correspond to interruptions in either of the two CGG repeat loci. Instead, exhaustive enumeration software is used to identify the correct genotype.

First, the software enumerates all possible genotypes for each of the two loci using the overall CGG repeat length and Anch T information. Next, the solutions are evaluated for self consistency and report compatibility. Self consistency asks whether the potential solution genotype has one or more consecutive AGG sequence and rejects any potential sequence having consecutive AGGs. Report compatibility asks whether the potential solution genotype is fully consistent with all data in the CE report. In other words, report compatibility asks whether a potential solution is consistent with the CGG locus length, Anch T, and Anch A data. The genotype that satisfies all three requirements is selected as the solution genotype.

Using the overall CGG repeat length and Anch T data shown in Table 2, the exhaustive enumeration program would generate sets of potential sequences for CGG loci 1 and 2, as shown in Tables 3 and 4.

TABLE 3

| Potential sequences for CGG locus 1 | |
|---|---|
| $(CGG)_{29}$ (SEQ ID NO: 4) | Corresponding to a genotype lacking interruptions |
| $(CGG)_{10}(AGG)(CGG)_{18}$ (SEQ ID NO: 5) | Corresponding to a genotype having one interruption at position {11} |
| $(CGG)_{19}(AGG)(CGG)_9$ (SEQ ID NO: 2) | Corresponding to a genotype having one interruption at position {20} |
| $(CGG)_{10}(AGG)(CGG)_8(AGG)(CGG)_9$ (SEQ ID NO: 6) | Corresponding to a genotype having two interruption at positions {11, 20} |

TABLE 4

| Potential sequences for CGG locus 2 | |
|---|---|
| $(CGG)_{52}$ (SEQ ID NO: 7) | Corresponding to a genotype lacking interruptions |

TABLE 4 -continued

Potential sequences for CGG locus 2

$(CGG)_{10}(AGG)(CGG)_{41}$ (SEQ ID NO: 3) Corresponding to a genotype having one interruption at position {11}

$(CGG)_{19}(AGG)(CGG)_{32}$ (SEQ ID NO: 8) Corresponding to a genotype having one interruption at position {20}

$(CGG)_{10}(AGG)(CGG)_{8}(AGG)(CGG)_{32}$ (SEQ ID NO: 9) Corresponding to a genotype having two interruption at positions {11, 20}

Combining Tables 3 and 4 generates a set of 16 potential genotypes derived from the CE data for the FMR1 gene having 2 CGG repeat loci, as shown in Table 5.

TABLE 5

$(CGG)_{29}$ (SEQ ID NO: 4)/$(CGG)_{52}$ (SEQ ID NO: 7)

$(CGG)_{29}$ (SEQ ID NO: 4)/$(CGG)_{10}(AGG)(CGG)_{41}$ (SEQ ID NO: 3)

$(CGG)_{29}$ (SEQ ID NO: 4)/$(CGG)_{19}(AGG)(CGG)_{32}$ (SEQ ID NO: 8)

$(CGG)_{29}$ (SEQ ID NO: 4)/$(CGG)_{10}(AGG)(CGG)_{8}(AGG)(CGG)_{32}$ (SEQ ID NO: 9)

$(CGG)_{10}(AGG)(CGG)_{18}$ (SEQ ID NO: 5)/$(CGG)_{52}$ (SEQ ID NO: 7)

$(CGG)_{10}(AGG)(CGG)_{18}$ (SEQ ID NO: 5)/$(CGG)_{10}(AGG)(CGG)_{41}$ (SEQ ID NO: 3)

$(CGG)_{10}(AGG)(CGG)_{18}$ (SEQ ID NO: 5)/$(CGG)_{19}(AGG)(CGG)_{32}$ (SEQ ID NO: 8)

$(CGG)_{10}(AGG)(CGG)_{18}$ (SEQ ID NO: 5)/$(CGG)_{10}(AGG)(CGG)_{8}(AGG)(CGG)_{32}$ (SEQ ID NO: 9)

$(CGG)_{19}(AGG)(CGG)_{9}$ (SEQ ID NO: 2)/$(CGG)_{52}$ (SEQ ID NO: 7)

$(CGG)_{19}(AGG)(CGG)_{9}$ (SEQ ID NO: 2)/$(CGG)_{10}(AGG)(CGG)_{41}$ (SEQ ID NO: 3)

$(CGG)_{19}(AGG)(CGG)_{9}$ (SEQ ID NO: 2)/$(CGG)_{19}(AGG)(CGG)_{32}$ (SEQ ID NO: 8)

$(CGG)_{19}(AGG)(CGG)_{9}$ (SEQ ID NO: 2)/$(CGG)_{10}(AGG)(CGG)_{8}(AGG)(CGG)_{32}$ (SEQ ID NO: 9)

$(CGG)_{10}(AGG)(CGG)_{8}(AGG)(CGG)_{9}$ (SEQ ID NO: 6)/$(CGG)_{52}$ (SEQ ID NO: 7)

TABLE 5 -continued $(CGG)_{10}(AGG)(CGG)_{8}(AGG)(CGG)_{9}$ (SEQ ID NO: 6)/$(CGG)_{10}(AGG)(CGG)_{41}$ (SEQ ID NO: 3)

$(CGG)_{10}(AGG)(CGG)_{8}(AGG)(CGG)_{9}$ (SEQ ID NO: 6)/$(CGG)_{19}(AGG)(CGG)_{32}$ (SEQ ID NO: 8)

$(CGG)_{10}(AGG)(CGG)_{8}(AGG)(CGG)_{9}$ (SEQ ID NO: 6)/$(CGG)_{10}(AGG)(CGG)_{8}(AGG)(CGG)_{32}$ (SEQ ID NO: 9)

Each of the genotypes in Table 5 is evaluated for self-consistency and report compatibility. For example, the first potential genotype ($(CGG)_{29}$ (SEQ ID NO: 4)/$(CGG)_{52}$ (SEQ ID NO: 7)) is self consistent since the genotype does not contain any contiguous AGG sequences. However, the genotype generates an Anch T of {null} and an Anch A of {null} because there are no AGG interruptions in either loci, which is not consistent with the Anch T of {11, 20} and Anch A of {10, 42} shown in the CE report. Thus, this potential solution is rejected as report incompatible. Similarly, the next potential solution, (($(CGG)_{29}$ (SEQ ID NO: 4)/$(CGG)_{10}(AGG)(CGG)_{41}$ (SEQ ID NO: 3)) is also self consistent but not report compatible, as it generates an Anch T of {11} and an Anch A of {42}. Thus, the software would also reject this potential solution as report incompatible. The software continues to examines each of the 16 potential genotypes and rejects all of them except for $(CGG)_{19}(AGG)(CGG)_{9}$ (SEQ ID NO: 2)/$(CGG)_{10}(AGG)(CGG)_{41}$ (SEQ ID NO: 3), which is self consistent and report compatible (it generates an Anch T of {11, 20} and an Anch A of {10, 42}, which correspond to the Anch A and Anch T data in the CE report). This sequence is identified as the solution genotype.

The preceding examples are intended to illustrate and in no way limit the present disclosure. Other embodiments of the disclosed devices and methods will be apparent to those skilled in the art from consideration of the specification and practice of the devices and methods disclosed herein.

What is claimed is:

1. A method of automated reconstruction of a genotype, comprising
   a) providing a sample from a patient, wherein the sample comprises a nucleic acid having at least one repeat or GC-rich region;
   b) amplifying a region of the nucleic acid comprising the at least one repeat or GC-rich region;
   c) measuring parameter information for the nucleic acid, wherein measuring the parameter information comprises measuring a total length of the at least one repeat or GC-rich region, a distance in the forward direction to any interruptions in the region, and a distance in the reverse direction to any interruptions in the region; and
   d) using an apparatus to conduct automated exhaustive enumeration on the parameter information to generate a reconstructed genotype, wherein exhaustive enumeration comprises
      i) using the total length of the at least one repeat or GC-rich region and either the distance in the forward direction to any interruptions in the region or the distance in the reverse direction to any interruptions in the region to generate a set of potential genotypes comprising all possible arrangements of the interruptions in the region; and
      ii) evaluating the set of potential genotypes to determine a solution genotype that satisfies all the parameter information.

2. The method of claim 1, wherein measuring the parameter information comprises a polymerase chain reaction step.

3. The methods of claim 1, wherein the apparatus comprises a processor and a memory device communicatively coupled to the processor, wherein the memory device has stored therein machine-executable instructions that, when executed by the processor, cause the processor to receive parameter information and to conduct an exhaustive enumeration analysis.

4. The methods of claim 1, further comprising confirming the reconstructed genotype by manually comparing the genotype to the parameter information, by performing a restriction digest, or by sequencing the nucleic acid having at least one repeat or GC-rich region.

5. The method of claim 1, wherein the genotype being reconstructed is the FMR1 or FMR2 gene or fragments thereof.

6. The method of claim 5, further comprising using the reconstructed genotype to detect a genotype associated with an FMR1 or FMR2 disorder in a patient, or to detect a risk of an FMR1 or FMR2 disorder in offspring of the patient.

7. The method of claim 6, wherein the FMR1 or FMR2 disorder is Fragile X Syndrome (FXS), Fragile X syndrome E (FRAXE), Fragile X-associated tremor/ataxia syndrome (FXTAS), fragile X-related primary ovarian insufficiency (FXPOI), or dopamine-responsive Parkinsonism.

8. The method of claim 1, wherein a genotype from a parent of the patient is not known.

9. A method of automated reconstruction of an FMR1 genotype, comprising
    a) providing a sample from a patient, wherein the sample comprises an FMR1 nucleic acid or a fragment thereof;
    b) amplifying a region of the FMR1 nucleic acid or fragment comprising at least one CGG repeat region;
    c) measuring parameter information for the FMR1 nucleic acid or fragment, wherein measuring the parameter information comprises measuring a total length of at least one CGG repeat region, a distance in the forward direction to any AGG interruptions in the CGG repeat region, and a distance in the reverse direction to any AGG interruptions in the CGG repeat region; and
    d) using an apparatus to conduct automated exhaustive enumeration on the parameter information to generate a reconstructed FMR1 genotype, wherein exhaustive enumeration comprises
        i) using the total length of the at least one CGG region and either the distance in the forward direction to any AGG interruptions in the CGG repeat region or the distance in the reverse direction to any AGG interruptions in the CGG repeat region to generate a set of potential genotypes comprising all possible arrangements of the AGG interruptions in the CGG repeat region; and
        ii) evaluating the set of potential genotypes to determine a solution genotype that satisfies all the parameter information.

10. The method of claim 9, wherein measuring the parameter information comprises polymerase chain reaction and capillary electrophoresis steps.

11. The methods of claim 9, wherein the apparatus comprises a processor and a memory device communicatively coupled to the processor, wherein the memory device has stored therein machine-executable instructions that, when executed by the processor, cause the processor to receive parameter information and to conduct an exhaustive enumeration analysis.

12. The method of claim 9, further comprising confirming the reconstructed FMR1 genotype by manually comparing the genotype to the parameter information, by performing a restriction digest, or by sequencing the FMR1 nucleic acid or fragment.

13. The method of claim 9, further comprising using the reconstructed FMR1 genotype to detect a genotype associated with an FMR1 disorder in a patient, or to detect a risk of an FMR1 disorder in offspring of the patient.

14. The method of claim 13, wherein the FMR1 disorder is Fragile X Syndrome (FXS), Fragile X-associated tremor/ataxia syndrome (FXTAS), fragile X-related primary ovarian insufficiency (FXPOI), or dopamine-responsive Parkinsonism.

15. The method of claim 9, wherein an FMR1 genotype from a parent of the patient is not known.

16. A method of detecting an FMR1 or FMR2 genotype associated with a disorder in a patient, or a risk of an FMR1 or FMR2 disorder in offspring of the patient, comprising
    a) providing a sample from a patient, wherein the sample comprises an FMR1 or FMR2 nucleic acid or fragment thereof;
    b) amplifying a region of the FMR1 or FMR2 nucleic acid or fragment comprising at least one repeat or GC-rich region;
    c) measuring parameter information for the FMR1 or FMR2 nucleic acid or fragment, wherein measuring the parameter information comprises measuring a total length of at least one repeat or GC-rich region, a distance in the forward direction to any interruptions in the region, and a distance in the reverse direction to any interruptions in the region;
    d) applying automated exhaustive enumeration to the parameter information to generate a reconstructed genotype, wherein exhaustive enumeration comprises
        i) using the total length of the at least one repeat or GC-rich region and either the distance in the forward direction to any interruptions in the region or the distance in the reverse direction to any interruptions in the region to generate a set of potential genotypes comprising all possible arrangements of the interruptions in the region; and
        ii) evaluating the set of potential genotypes to determine a solution genotype that satisfies all the parameter information; and
    e) using the reconstructed genotype to detect an FMR1 or FMR2 genotype associated with a disorder in a patient, or to detect a risk of an FMR1 or FMR2 disorder in offspring of the patient.

17. The method of claim 16, wherein the FMR1 or FMR2 disorder is Fragile X Syndrome (FXS), Fragile X syndrome E (FRAXE), Fragile X-associated tremor/ataxia syndrome (FXTAS), fragile X-related primary ovarian insufficiency (FXPOI), or dopamine-responsive Parkinsonism.

18. The method of claim 16, wherein an FMR1 or FMR2 genotype from a parent of the patient is not known.

19. The method of claim 6, wherein the reconstructed genotype is used to detect a risk of an FMR1 or FMR2 disorder in offspring of the patient.

20. The method of claim 13, wherein the reconstructed genotype is used to detect a risk of an FMR1 disorder in offspring of the patient.

21. The method of claim 16, wherein the reconstructed genotype is used to detect a risk of an FMR1 or FMR2 disorder in offspring of the patient.

22. A method of treating a patient for an FMR1 or FMR2 disorder, the method comprising A) detecting an FMR1 or FMR2 genotype associated with a disorder in a patient, comprising
   i) providing a sample from a patient, wherein the sample comprises an FMR1 or FMR2 nucleic acid or fragment thereof;
   ii) amplifying a region of the FMR1 or FMR2 nucleic acid or fragment comprising at least one repeat or GC-rich region;
   iii) measuring parameter information for the FMR1 or FMR2 nucleic acid or fragment, wherein measuring the parameter information comprises measuring a total length of at least one repeat or GC-rich region, a distance in the forward direction to any interruptions in the region, and a distance in the reverse direction to any interruptions in the region;
   iv) applying automated exhaustive enumeration to the parameter information to generate a reconstructed genotype, wherein exhaustive enumeration comprises
      a) using the total length of the at least one repeat or GC-rich region and either the distance in the forward direction to any interruptions in the region or the distance in the reverse direction to any interruptions in the region to generate a set of potential genotypes comprising all possible arrangements of the interruptions in the region; and
      b) evaluating the set of potential genotypes to determine a solution genotype that satisfies all the parameter information; and
   v) using the reconstructed genotype to detect an FMR1 or FMR2 genotype associated with a disorder in a patient; and
B) administering a treatment for an FMR1 or FMR2 disorder if a disorder is detected.

23. A method of treating a patient for a risk of an FMR1 or FMR2 disorder in offspring of the patient, the method comprising
   A) detecting a risk of an FMR1 or FMR2 disorder in offspring of the patient, comprising
      i) providing a sample from a patient, wherein the sample comprises an FMR1 or FMR2 nucleic acid or fragment thereof;
      ii) amplifying a region of the FMR1 or FMR2 nucleic acid or fragment comprising at least one repeat or GC-rich region;
      iii) measuring parameter information for the FMR1 or FMR2 nucleic acid or fragment, wherein measuring the parameter information comprises measuring a total length of at least one repeat or GC-rich region, a distance in the forward direction to any interruptions in the region, and a distance in the reverse direction to any interruptions in the region;
      iv) applying automated exhaustive enumeration to the parameter information to generate a reconstructed genotype, wherein exhaustive enumeration comprises
         a) using the total length of the at least one repeat or GC-rich region and either the distance in the forward direction to any interruptions in the region or the distance in the reverse direction to any interruptions in the region to generate a set of potential genotypes comprising all possible arrangements of the interruptions in the region; and
         b) evaluating the set of potential genotypes to determine a solution genotype that satisfies all the parameter information; and
      v) using the reconstructed genotype to detect a risk of an FMR1 or FMR2 disorder in offspring of the patient; and
   B) administering a treatment if a risk of an FMR1 or FMR2 disorder in offspring of the patient is detected.

24. A method of treating a patient for an FMR1 or FMR2 disorder, comprising administering a treatment for an FMR1 or FMR2 disorder to a patient having the disorder, wherein the patient has been characterized as having the disorder by a method comprising
   i) providing a sample from a patient, wherein the sample comprises an FMR1 or FMR2 nucleic acid or fragment thereof;
   ii) amplifying a region of the FMR1 or FMR2 nucleic acid or fragment comprising at least one repeat or GC-rich region;
   iii) measuring parameter information for the FMR1 or FMR2 nucleic acid or fragment, wherein measuring the parameter information comprises measuring a total length of at least one repeat or GC-rich region, a distance in the forward direction to any interruptions in the region, and a distance in the reverse direction to any interruptions in the region;
   iv) applying automated exhaustive enumeration to the parameter information to generate a reconstructed genotype, wherein exhaustive enumeration comprises
      a) using the total length of the at least one repeat or GC-rich region and either the distance in the forward direction to any interruptions in the region or the distance in the reverse direction to any interruptions in the region to generate a set of potential genotypes comprising all possible arrangements of the interruptions in the region; and
      b) evaluating the set of potential genotypes to determine a solution genotype that satisfies all the parameter information; and
   v) using the reconstructed genotype to characterize the patient by detecting an FMR1 or FMR2 genotype associated with a disorder.

25. A method of treating a patient for a risk of having offspring with an FMR1 or FMR2 disorder, comprising administering a treatment to a patient identified as being at risk, wherein the patient has been characterized as being at risk by a method comprising
   i) providing a sample from a patient, wherein the sample comprises an FMR1 or FMR2 nucleic acid or fragment thereof;
   ii) amplifying a region of the FMR1 or FMR2 nucleic acid or fragment comprising at least one repeat or GC-rich region;
   iii) measuring parameter information for the FMR1 or FMR2 nucleic acid or fragment, wherein measuring the parameter information comprises measuring a total length of at least one repeat or GC-rich region, a distance in the forward direction to any interruptions in the region, and a distance in the reverse direction to any interruptions in the region;
   iv) applying automated exhaustive enumeration to the parameter information to generate a reconstructed genotype, wherein exhaustive enumeration comprises
      a) using the total length of the at least one repeat or GC-rich region and either the distance in the forward direction to any interruptions in the region or the distance in the reverse direction to any interruptions in the region to generate a set of potential genotypes comprising all possible arrangements of the interruptions in the region; and b) evaluating the set of potential genotypes to determine a solution genotype that satisfies all the parameter information; and v) using the reconstructed genotype to characterize the risk of having offspring with an FMR1 or FMR2 disorder.

* * * * *

SEQUENCE LISTING

<160> NUMBER OF SEQ ID NOS: 10

<210> SEQ ID NO 1
<211> LENGTH: 69
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
cggcggcggc ggaggcggcg gcggcggcgg cggcggcggc ggcggcggcg gaggcggcgg    60
cggcggcgg                                                            69

<210> SEQ ID NO 2
<211> LENGTH: 87
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 2
cggcggcggc ggcggcggcg gcggcggcgg cggcggcggc ggcggcggcg gcggcggagg    60
cggcggcggc ggcggcggcg gcggcgg                                        87

<210> SEQ ID NO 3
<211> LENGTH: 156
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 3
cggcggcggc ggcggcggcg gcggcggcgg aggcggcggc ggcggcggcg gcggcggcgg    60
cggcggcggc ggcggcggcg gcggcggcgg cggcggcggc ggcggcggcg gcggcggcgg   120
cggcggcggc ggcggcggcg gcggcggcgg cggcgg                             156

<210> SEQ ID NO 4
<211> LENGTH: 87
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 4
cggcggcggc ggcggcggcg gcggcggcgg cggcggcggc ggcggcggcg gcggcggcgg    60
cggcggcggc ggcggcggcg gcggcgg                                        87

<210> SEQ ID NO 5
<211> LENGTH: 87
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 5
cggcggcggc ggcggcggcg gcggcggcgg aggcggcggc ggcggcggcg gcggcggcgg    60
cggcggcggc ggcggcggcg gcggcgg                                        87

<210> SEQ ID NO 6
<211> LENGTH: 87
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 6
cggcggcggc ggcggcggcg gcggcggcgg aggcggcggc ggcggcggcg gcggcggagg    60
cggcggcggc ggcggcggcg gcggcgg                                        87

<210> SEQ ID NO 7

```
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7
cggcggcggc ggcggcggcg gcggcggcgg cggcggcggc ggcggcggcg gcggcggcgg        60
cggcggcggc ggcggcggcg gcggcggcgg cggcggcggc ggcggcggcg gcggcggcgg       120
cggcggcggc ggcggcggcg gcggcggcgg cggcgg                                 156

<210> SEQ ID NO 8
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
cggcggcggc ggcggcggcg gcggcggcgg cggcggcggc ggcggcggcg gcggcggagg        60
cggcggcggc ggcggcggcg gcggcggcgg cggcggcggc ggcggcggcg gcggcggcgg       120
cggcggcggc ggcggcggcg gcggcggcgg cggcgg                                 156

<210> SEQ ID NO 9
<211> LENGTH: 156
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9
cggcggcggc ggcggcggcg gcggcggcgg aggcggcggc ggcggcggcg gcggcggagg        60
cggcggcggc ggcggcggcg gcggcggcgg cggcggcggc ggcggcggcg gcggcggcgg       120
cggcggcggc ggcggcggcg gcggcggcgg cggcgg                                 156

<210> SEQ ID NO 10
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
ccccgccccg cg                                                            12
```